United States Patent

Sahlén

[11] Patent Number: 5,730,024
[45] Date of Patent: Mar. 24, 1998

[54] TEST PROBE FOR MEASUREMENT OF MOISTURE IN STRUCTURAL MATERIAL

[75] Inventor: Nicklas Sahlén, Dalby, Sweden

[73] Assignee: Sahlens Fuktkontroll, Malmo, Sweden

[21] Appl. No.: 387,718

[22] PCT Filed: Aug. 17, 1993

[86] PCT No.: PCT/SE93/00682

§ 371 Date: Feb. 16, 1995

§ 102(e) Date: Feb. 16, 1995

[87] PCT Pub. No.: WO94/04910

PCT Pub. Date: Mar. 3, 1994

[30] Foreign Application Priority Data

Aug. 17, 1992 [SE] Sweden .................. 9202358
Jan. 11, 1993 [SE] Sweden .................. 9300042

[51] Int. Cl.⁶ ................... G01N 27/12; G01N 33/38
[52] U.S. Cl. ................... 73/73; 324/694
[58] Field of Search ................ 73/73, 335.05; 324/694, 696, 724, 439, 446

[56] References Cited

U.S. PATENT DOCUMENTS

| | | | |
|---|---|---|---|
| 2,754,378 | 7/1956 | Ohlheiser | 73/335.05 |
| 2,941,174 | 6/1960 | Richards | 73/73 |
| 3,430,486 | 3/1969 | Richards | 73/73 |
| 3,680,364 | 8/1972 | Carrier | 73/73 |
| 4,137,931 | 2/1979 | Hasenbeck | 73/73 |
| 4,242,906 | 1/1981 | Briscoe et al. | 73/73 |
| 4,837,499 | 6/1989 | Scherer, III | 73/73 |
| 4,862,730 | 9/1989 | Crosby | 73/38 |
| 5,382,908 | 1/1995 | Forsstrom et al. | 324/439 |
| 5,568,747 | 10/1996 | Lloyd | 73/73 |

FOREIGN PATENT DOCUMENTS

| | | |
|---|---|---|
| 3641875 | 6/1988 | Germany. |
| 2245976 | 1/1992 | United Kingdom. |
| 9011513 | 10/1990 | WIPO. |

OTHER PUBLICATIONS

Studies on Concrete Technology, Dedicated to Sven G. Bergstrom, Swedish Cement and Concrete Research Institute, Stockholm, pp. 217–225, Dec. 1979.

*Primary Examiner*—William A. Cuchlinski, Jr.
*Assistant Examiner*—Andrew Hirshfeld
*Attorney, Agent, or Firm*—Ostrolenk, Faber, Gerb & Soffen, LLP

[57] ABSTRACT

The invention relates to a test probe (1) primarily intended to be applied in structural material (2) during the production and/or building stage or when water damage has occured in a building and in which moisture measurement can be done undisturbed from outer factors in following the drying out process of built in moisture or other inconvenient, supplied moisture which can cause troubles in the form of mold and/or damages caused by putrefaction, as well as damages on floor coverings and other structural elements. The test probe (1) comprises an active part (3) of a hygroscopic material which is enclosed in an outer, mechanical cover (4), said cover has that property to allow passage of water steam, but prevents passage of water in liquid.

13 Claims, 2 Drawing Sheets

TEST PROBE FOR MEASUREMENT OF MOISTURE IN STRUCTURAL MATERIAL

BACKGROUND OF THE INVENTION

The present invention relates to a test probe which primarily is intended for being applied in structural materials during production and/or building activity or when water damage has occured in a building and by which test probe moisture measurement can be performed undisturbed from outer factors in following of the drying up process of built in moisture or other not suitable, supplied moisture which can cause inconveniences in the form of mould and/or damage caused by putrefactions, as well as damage of floor coverings and other structural elements.

At present the problem of building moisture within the building sector is a scourge which besides the fact that it causes many practical problems, e.g. origin of mould and other "sick house" problems, is the source of very wide and in itself unnecessary increases in prices. Today the idea of the used technique to reveal the departure of building moisture is that you drill a hole in the building element in question to a desired depth, where you want to determine the moisture level. A transmitter is then inserted into the hole, by aid of which you can read on an after-connected instrument the temperature and the relative humidity of the material (RF %). Several types of transmitters are used and for all concern the unexactness proportionately is as large as about ±3–5% RF. The technique of this measuring method is relatively complicated and requires good knowledge in technics of measurement, which only in exceptional cases exsists within the building sector.

The object of the present invention is to provide a test probe, by which the problems exsisting in the transmitter which now are present on the market have been eliminated. The distinguishing features of the invention are set forth in the claims mentioned below.

Thanks to the invention, one has now achieved a test probe which in an excellent way fulfils its purpose, and at the same time, is both cheap and easy to produce. By aid of the test probe according to the invention it is possible to already from the beginning, i.e. from the stage of production of a structural work, to follow the development of the drying up of built in moisture, commonly called as building moisture, in most of the building elements, that a structural work consists of. Further the invention decreases the necessary knowledge of techniques of measurement, which are required up to a minimum and minimizes sources of errors which otherwise can occur principally in that its active part is able to be applied in the building element itself during the production stage on the building site. This fact makes it possible to measure the moisture state undisturbed by outer factors, where you really want to do it and whenever you want. Both the actual test probe as well as the indicating instrument are in fact much cheaper than the set of apparatus which today are present on the building market intended for similar applications. The test probe according to the present invention has an application range of a high quality in determination of actual moisture stage at a low price.

BRIEF DESCRIPTION OF THE DRAWINGS

The invention will now be further described below by aid of a preferred embodiment with reference to the drawings enclosed, in which FIG. 1 schematically illustrates a test probe according to the invention which is cast into a structural work and FIG. 2 schematically illustrates another embodiment of a test probe according to the invention in a condition cast into its position.

DESCRIPTION OF THE INVENTION

Figure 1:
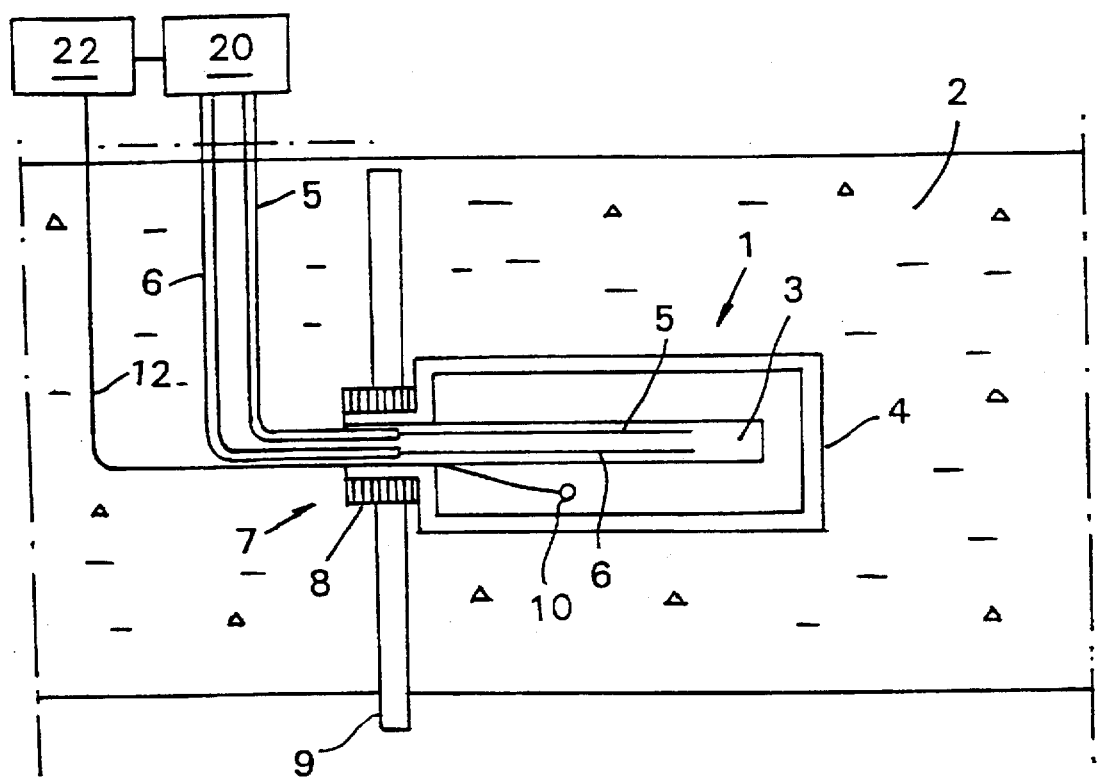

As illustrated in FIG. 1 a preferred, first embodiment of a test probe 1 according to the present invention consists of such a formation which is fixable in a structural material 2 during the production stage. It is, in other words, possible to be cast into e.g. concrete directly which is unique within the moisture measurement range. The test probe 1, which has such a quality that it can absorb and emit moisture in steam phase but not in liquid phase, includes an active part 3 consisting of a hygroscopic material, said part is enclosed in an outer, mechanical cover 4. The test probe 1 has that quality owing to that the cover 4 consists of an expanded plastic designed in such a way that water vapour can pass through it, but not water in a liquid phase. The cover 4 is also intended to prevent a break down of the active part 3 of the test probe 1, which is exposed to pressure during casting into the concrete. The mechanical cover 4 is continuous as to its formation and is provided with a supporting means 7 in one end of the same in the form of threaded washers 8 for tightening of the test probe 1 in a position fixing means 9 for a temporary fixing of the same in connection with concrete casting. The position fixing means 9 is also threaded, and therefore can be moved within the washers 8 to fix the cover 4 between the means 9. Alternatively, the means 9 can be fixed in place, and the washers 8 can be moved along the means 9 to fix the cover 4 between the washers 8.

The active part 3 of the test probe 1 which consists of a hygroscopic material comprises in the example described a round bar of wood having a diameter of about 6 mm. This material adjusts its relative humidity RF % to the relative atmospheric humidity RF % of the ambient material. Two unisolated electrodes 5 and 6 are inserted into the active part 3 thereby making it possible to read the actual relative atmospheric humidity RF % of the test probe 1. These electrodes 5,6 are stuck into the active part 3 of the test probe 1 a distance, which in the example illustrated amounts to about 3–6 times the diameter of the active part 3. Those parts of the electrodes 5,6 which extend from the test probe 1 and through the concrete 2 and further to a resistance meter 20 are isolated. On the electrodes 5,6 the electrical resistance which occurs between them, is measured, at actual moisture level. The resistance is indicated with a conventional resistance meter at different moisture levels.

Since the magnitude of the resistance also is dependent of the temperature at the measuring place, it is measured by a temperature indicator in the form of a thermistor 10 which is situated between the active part 3 of the test probe and the mechanical cover 4 and which is connected to a measuring equipment not illustrated in the drawing by a cable 12. In reading a temperature other than 20° C., the resistance reading is compensated (corrected) by aid of a micro-processor 22.

The instrument also can be equipped with an indicator which indicates the temperature measured in °C. The conversion of the temperature corrected resistance reading to relative humidity RF % occurs in that a resistance values for moisture between 75–97% RF reference are fed into said micro-processor. The temperature corrected resistance reading is compared to the resistance values fed into the micro-processor to obtain the relative humidity associated with the temperature corrected resistance reading.

Figure 2:
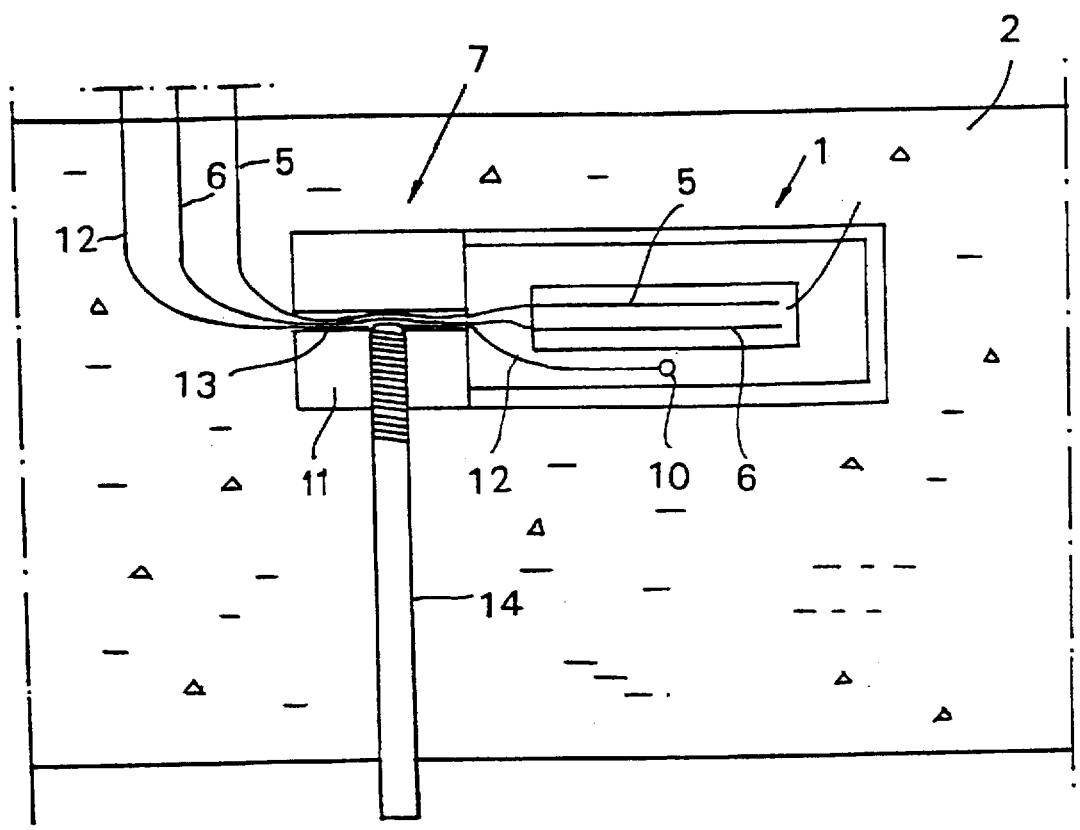

In FIG. 2 is illustrated a modified embodiment of the test probe 1 according to the present invention. Here it is primarily the fixing itself of the test probe 1 in place which is different. Otherwise the construction almost corresponds to that test probe illustrated in FIG. 1. However, the supporting means 7 is here formed as a means of attachment 11. The electrodes 5 and 6 and the transmitter cable 12 extended through this from the thermistor 10 by an opening 13. A round bar 14 is by its threading into the attachment means 11 intended both to unload said cables 5,6 and 12 from tension and to fix the test probe 1 during its casting into the structural material 2 which consists of concrete.

I claim:

1. A test probe assembly applied to structural material characterized in that a test probe is applied within the structural material and comprises an active part (3) consisting of a hygroscopic material, mostly enclosed in an outer mechanical cover (4) having a quality of allowing passage of water vapor but not liquid water and said cover (4) consists of a housing of expanded plastics resistant to pressure so as to allow casting of the test probe (1) into the structural material, at least two unisolated electrodes (5, 6) provided in the active part (3), said electrodes in an isolated state extending from the test probe (1) through and out from the structural material (2) and to a resistance meter means for measuring electrical resistance which is present in the active part (3) between the electrodes (5,6), and at least one thermistor (10) located between the active part (3) and the mechanical cover (4) and which by a connecting cable is connected to a microprocessor programmed to compensate the resistance reading as a function of a measured temperature and convert said temperature compensated resistance reading to relative humidity (RF %) by comparison to reference resistance values for humidity between 75–97% RF in the micro processor, and an indicator to display the value of the relative humidity determined.

2. A test probe assembly according to claim 1, characterized in that the active part (3) consists of a round bar of wood having a length of about 3–6 times its diameter.

3. A test probe assembly according to claim 2, characterized in that the mechanical cover (4) is elongated and has one end provided with a supporting means (7) in the form of a threaded washer (8) movable relative to a fixing rod (9).

4. A test probe assembly according to claim 3, characterized in that the round bar of wood has a diameter of 6 mm.

5. A test probe assembly according to claim 2, characterized in that the mechanical cover (4) has one end fixed to a supporting means (7) in the form of an attachment means (11), through which the electrodes (5,6) and the connecting cable (12) from the thermistor (10) extend via an opening (13) out to and through the structural material (2), and in said attachment means (11) a position fixing means in the form of a round bar (14) is threaded, both to unload the electrodes and the connecting cable (12) in the opening (13) in tension and also to fix the test probe (1) during its casting into the structural material (2).

6. A test probe assembly according to claim 5, characterized in that the round bar of wood has a diameter of 6 mm.

7. A test probe assembly according to claim 2, characterized in that the round bar of wood has a diameter of 6 mm.

8. A test probe according to claim 1, characterized in that the unisolated electrodes (5,6) extend into the active part (3) a distance, which is at least ⅓ of its total, effective length.

9. A test probe assembly according to claim 8, characterized in that the mechanical cover (4) is elongated and has one end provided with a supporting means (7) in the form of a threaded washer (8) movable relative to a fixing rod (9).

10. A test probe assembly according to claim 8, characterized in that the mechanical cover (4) has one end fixed to a supporting means (7) in the form of an attachment means (11), through which the electrodes (5,6) and the connecting cable (12) from the thermistor (10) extend via an opening (13) out to and through the structural material (2), and in said attachment means (11) a position fixing means in the form of a round bar (14) is threaded, both to unload the electrodes and the connecting cable (12) in the opening (13) in tension and also to fix the test probe (1) during its casting into the structural material (2).

11. A test probe according to claim 1 characterized in that the mechanical cover (4) is elongated and has one end provided with a supporting means (7) in the form of a threaded washer (8) movable relative to a fixing rod (9).

12. A test probe assembly according to claim 1 characterized in that the mechanical cover (4) has one end fixed to a supporting means (7) in the form of an attachment means (11), through which the electrodes (5,6) and the connecting cable (12) from the thermistor (10) extend via an opening (13) out to and through the structural material (2), and in said attachment means (11) a position fixing means in the form of a round bar (14) is threaded, both to unload the electrodes and the connecting cable (12) in the opening (13) in tension and also to fix the test probe (1) during its casting into the structural material (2).

13. A test probe assembly according to claim 1, wherein the structural material is concrete.

* * * * *